US012781167B2

(12) United States Patent
Martin et al.

(10) Patent No.: US 12,781,167 B2
(45) Date of Patent: Nov. 3, 2026

(54) MICROCAVITY PLATE

(71) Applicant: CORNING INCORPORATED, Corning, NY (US)

(72) Inventors: Gregory Roger Martin, Acton, ME (US); Allison Jean Tanner, Portsmouth, NH (US)

(73) Assignee: CORNING INCORPORATED, Corning, NY (US)

(*) Notice: Subject to any disclaimer, the term of this patent is extended or adjusted under 35 U.S.C. 154(b) by 709 days.

(21) Appl. No.: 18/031,774

(22) PCT Filed: Oct. 27, 2021

(86) PCT No.: PCT/US2021/056736
§ 371 (c)(1),
(2) Date: Apr. 13, 2023

(87) PCT Pub. No.: WO2022/093883
PCT Pub. Date: May 5, 2022

(65) Prior Publication Data
US 2023/0383226 A1 Nov. 30, 2023

Related U.S. Application Data

(60) Provisional application No. 63/107,663, filed on Oct. 30, 2020.

(51) Int. Cl.
*C12M 1/00* (2006.01)
*C12M 1/32* (2006.01)
(Continued)

(52) U.S. Cl.
CPC ............ *C12M 23/16* (2013.01); *C12M 23/12* (2013.01); *C12M 23/20* (2013.01); *C12M 23/38* (2013.01);
(Continued)

(58) Field of Classification Search
CPC ...... C12M 23/16; C12M 23/12; C12M 23/20; C12M 23/38; C12M 41/46; C12N 5/0062; C12N 2513/00
See application file for complete search history.

(56) References Cited

U.S. PATENT DOCUMENTS 2,947,116 A 8/1960 Wilton et al.
3,630,849 A 12/1971 David et al.
(Continued)

FOREIGN PATENT DOCUMENTS

AU 2004256209 A1 1/2005
CA 2558946 A1 1/2005
(Continued)

OTHER PUBLICATIONS

Weegman et al, "Nutrient Regulation By Continuous Feeding Removes Limitations on Cell Yield in the Large-Scale Expansion of Mammalian Cell Spheroids"; PLOS ONE, 2013, vol. 8, Issue 10, e76611, 10 Pages.
(Continued)

*Primary Examiner* — Liban M Hassan

(57) ABSTRACT

Microcavity plates (10) comprise a microcavity substrate and a base (303) comprising a bottom grid comprising a plurality of grid segments arranged in ordered rows and columns to form a plurality of openings, and an open well (307) comprising a plurality of sidewalls (309) extending vertically from a perimeter of the bottom grid. The microcavity substrate comprises a plurality of microcavities (315) arranged in ordered rows and columns that align with the plurality of openings in the bottom grid, each microcavity comprising a cavity disposed within an opening of the bottom grid. The microcavity plate may further comprise an upper grid (405) for placement on top of the bottom grid delineating the ordered rows and columns of the base.

25 Claims, 7 Drawing Sheets

(51) Int. Cl.
*C12M 1/34* (2006.01)
*C12M 3/06* (2006.01)
*C12N 5/00* (2006.01)

(52) U.S. Cl.
CPC .......... *C12M 41/46* (2013.01); *C12N 5/0062* (2013.01); *C12N 2513/00* (2013.01)

(56) References Cited

U.S. PATENT DOCUMENTS 4,382,685 A 5/1983 Pearson
4,461,836 A 7/1984 Von Froreich
4,498,785 A 2/1985 De Bruyne
4,534,656 A 8/1985 De Bruyne
4,670,396 A 6/1987 Bear et al.
4,760,028 A 7/1988 De Bruyne et al.
4,927,764 A 5/1990 Lyman et al.
4,980,293 A 12/1990 Jeffs
5,047,347 A 9/1991 Cline
5,151,366 A 9/1992 Serkes et al.
5,171,994 A 12/1992 Bahraman
5,171,995 A 12/1992 Gast et al.
5,240,854 A 8/1993 Berry et al.
5,272,084 A 12/1993 O'Connell et al.
5,319,436 A 6/1994 Manns et al.
5,374,557 A 12/1994 Verma
5,398,837 A 3/1995 Degrassi
5,487,872 A 1/1996 Hafeman et al.
5,554,536 A 9/1996 Rising
5,587,321 A 12/1996 Smith et al.
5,598,262 A 1/1997 Jutard et al.
5,665,562 A 9/1997 Cook
5,693,537 A 12/1997 Wilson et al.
5,707,869 A 1/1998 Wolf et al.
5,710,043 A 1/1998 Pay
5,736,397 A 4/1998 Garcia et al.
5,759,494 A 6/1998 Szlosek
5,766,949 A 6/1998 Liau et al.
5,772,905 A 6/1998 Chou
5,783,440 A 7/1998 Stevens
5,792,653 A 8/1998 Weibezahn et al.
5,858,309 A 1/1999 Mathus et al.
5,972,694 A 10/1999 Mathus
6,030,829 A 2/2000 Dannoux et al.
6,039,972 A 3/2000 Barlow et al.
6,306,646 B1 10/2001 Saad et al.
6,348,999 B1 2/2002 Summersgill et al.
6,514,464 B1 2/2003 Knebel
6,521,451 B2 2/2003 Potter
6,567,675 B1 5/2003 Rosen et al.
6,767,607 B2 7/2004 Tanner et al.
6,811,752 B2 11/2004 Barbera-Guillem
6,908,767 B2 6/2005 Bader
6,987,019 B1 1/2006 Rogalsky
7,470,424 B2 12/2008 Kataoka et al.
7,547,547 B2 6/2009 Dang et al.
7,674,346 B2 3/2010 Clements et al.
7,687,262 B2 3/2010 Cattadoris
7,691,369 B2 4/2010 Kataoka et al.
7,727,759 B2 6/2010 Ozawa et al.
7,745,209 B2 6/2010 Martin et al.
7,745,210 B2 6/2010 Martin
7,800,749 B2 9/2010 Leblanc et al.
7,897,379 B2 3/2011 Kenney et al.
7,919,319 B2 4/2011 Jervis et al.
8,053,230 B2 11/2011 Whittlinger
8,143,053 B2 3/2012 Yerbic
8,148,152 B2 4/2012 Kolossov et al.
8,158,426 B2 4/2012 Wilson et al.
8,158,427 B2 4/2012 Wilson et al.
8,163,537 B2 4/2012 Martin et al.
8,168,432 B2 5/2012 Wilson et al.
8,178,345 B2 5/2012 Bennett et al.
8,273,572 B2 9/2012 Martin et al.
8,318,479 B2 11/2012 Domansky et al.
8,415,144 B2 4/2013 Wilson et al.
8,470,589 B2 6/2013 Martin et al.
D685,497 S 7/2013 Kenney et al.
8,486,692 B2 7/2013 Simon
8,597,597 B2 12/2013 Deutsch et al.
8,617,879 B2 12/2013 Yu et al.
8,697,443 B2 4/2014 Wilson et al.
8,759,017 B2 6/2014 Owen et al.
8,778,669 B2 7/2014 Lacey et al.
8,846,399 B2 9/2014 Martin et al.
8,906,685 B2 12/2014 Takayama et al.
8,932,544 B2 1/2015 Mueller et al.
9,039,883 B2 5/2015 Guerrieri et al.
9,040,293 B2 5/2015 Gulzow et al.
9,045,721 B2 6/2015 Martin et al.
9,068,281 B2 6/2015 Wu et al.
9,126,199 B2 9/2015 Moritz et al.
9,169,460 B2 10/2015 Cecchi
D748,812 S 2/2016 Kenney et al.
9,260,684 B1 2/2016 Egeler et al.
9,260,695 B2 2/2016 Crowley et al.
9,389,187 B2 7/2016 Furnas
9,436,990 B2 9/2016 Otani et al.
9,493,733 B2 11/2016 Giles
9,494,577 B2 11/2016 Mcgarr et al.
9,573,128 B1 2/2017 McClelland
9,587,213 B2 3/2017 Morgan et al.
9,636,680 B2 5/2017 Fattinger et al.
9,732,317 B2 8/2017 Wilson
9,790,465 B2 10/2017 Bennett et al.
9,845,451 B2 12/2017 Martin et al.
9,862,918 B2 1/2018 Ito
9,933,373 B2 4/2018 Vild et al.
10,067,065 B1 9/2018 Alam et al.
10,254,274 B2 4/2019 Miklas et al.
11,441,121 B2 9/2022 Bennett et al.
11,613,722 B2 3/2023 Martin et al.
2002/0022219 A1 2/2002 Clements et al.
2002/0172621 A1 11/2002 Barbera-Guillem
2003/0031829 A1 2/2003 Tanner et al.
2003/0104494 A1 6/2003 Ravkin et al.
2003/0183958 A1 10/2003 Goff et al.
2003/0186217 A1 10/2003 Bader
2003/0205511 A1 11/2003 Olivier et al.
2003/0215941 A1 11/2003 Campbell et al.
2004/0091397 A1 5/2004 Picard
2004/0101955 A1 5/2004 Whitley
2004/0125266 A1 7/2004 Miyauchi et al.
2004/0216835 A1 11/2004 Tanner et al.
2004/0259242 A1 12/2004 Malinge et al.
2004/0259423 A1 12/2004 Elbaz et al.
2005/0032208 A1 2/2005 Oh et al.
2005/0047971 A1 3/2005 Clements et al.
2005/0074873 A1 4/2005 Shanler et al.
2005/0112030 A1 5/2005 Gaus
2005/0116717 A1 6/2005 Dransfield et al.
2005/0147959 A1 7/2005 Frondoza et al.
2006/0110822 A1 5/2006 Robbins et al.
2006/0234370 A1 10/2006 Korpinen et al.
2006/0252044 A1 11/2006 Okumura et al.
2006/0292654 A1 12/2006 Reardon
2007/0178441 A1 8/2007 Li
2007/0216897 A1 9/2007 Sonda
2008/0003671 A1 1/2008 Martin
2008/0009027 A1 1/2008 Fraker et al.
2008/0044312 A1* 2/2008 Malito .................. B01L 3/0293
422/68.1
2008/0118974 A1 5/2008 Martin et al.
2008/0206857 A1 8/2008 Kenney et al.
2008/0268515 A1 10/2008 Cullimore et al.
2008/0297784 A1 12/2008 Leblanc et al.
2008/0299649 A1 12/2008 Martin et al.
2008/0300278 A1 12/2008 Torrens et al.
2009/0017540 A1 1/2009 Nishio et al.
2009/0018033 A1 1/2009 Morgan et al.
2009/0029462 A1 1/2009 Beardsley et al.
2009/0037293 A1 2/2009 Unger et al.
2009/0170190 A1 7/2009 Nishi et al.
2009/0191620 A1 7/2009 Martin et al.
2009/0288963 A1 11/2009 Guerrieri et al.

(56) References Cited

U.S. PATENT DOCUMENTS

2009/0298164 A1 12/2009 Cattadoris et al.
2009/0298166 A1 12/2009 Fang et al.
2010/0055774 A1 3/2010 Wilson
2010/0068793 A1 3/2010 Ungrin et al.
2010/0074515 A1 3/2010 Zhao et al.
2010/0093075 A1 4/2010 Rolf
2010/0112014 A1 5/2010 Gilbert et al.
2010/0112684 A1 5/2010 Lee et al.
2010/0119418 A1 5/2010 Clements et al.
2010/0170790 A1 7/2010 Takahashi et al.
2010/0190197 A1 7/2010 Martin et al.
2010/0197013 A1 8/2010 Kamp et al.
2010/0247386 A1 9/2010 Deutsch et al.
2010/0273258 A1 10/2010 Lannutti et al.
2010/0296084 A1 11/2010 Berg et al.
2010/0297600 A1 11/2010 Cecchi
2011/0086375 A1 4/2011 Ungrin et al.
2011/0097790 A1 4/2011 Yerbic
2011/0104730 A1 5/2011 Larsen et al.
2011/0129923 A1 6/2011 Wilson et al.
2011/0229961 A1 9/2011 Higashi et al.
2012/0064627 A1 3/2012 Khine et al.
2012/0107926 A1* 5/2012 Yu .......................... C12M 29/10
435/325
2012/0129208 A1 5/2012 Khine et al.
2012/0129257 A1 5/2012 Yu et al.
2012/0219572 A1 8/2012 Prockop et al.
2013/0052331 A1 2/2013 Kram et al.
2013/0122539 A1 5/2013 Li et al.
2013/0122580 A1 5/2013 Tsukada et al.
2013/0143254 A1 6/2013 Thomas et al.
2013/0164848 A1 6/2013 Munaka et al.
2013/0203159 A1 8/2013 Itoh et al.
2013/0344598 A1 12/2013 Nistor
2014/0004086 A1 1/2014 Peak
2014/0027784 A1 1/2014 Wada et al.
2014/0099717 A1 4/2014 Fraker et al.
2014/0106394 A1 4/2014 Ko et al.
2014/0106452 A1 4/2014 Vukasinovic
2014/0120573 A1 5/2014 Tavana et al.
2014/0178992 A1 6/2014 Nakashima et al.
2014/0221225 A1 8/2014 Danen et al.
2014/0226004 A1 8/2014 Son et al.
2014/0227784 A1 8/2014 Ejiri et al.
2014/0240489 A1 8/2014 Furnas
2014/0315296 A1 10/2014 Wilson
2014/0322806 A1 10/2014 Bennett et al.
2015/0004686 A1 1/2015 Goral et al.
2015/0064738 A1 3/2015 Tsukada et al.
2015/0072405 A1 3/2015 Ito
2015/0184119 A1 7/2015 Tsukada et al.
2015/0247112 A1 9/2015 Orr et al.
2016/0003796 A1 1/2016 Kranbuehl
2016/0017267 A1 1/2016 Hansen et al.
2016/0040120 A1 2/2016 Gottwald et al.
2016/0137962 A1 5/2016 Ejiri et al.
2016/0194588 A1 7/2016 Guenat et al.
2016/0216250 A1 7/2016 Ritter et al.
2016/0250631 A1 9/2016 Kang et al.
2017/0067009 A1 3/2017 Sloane et al.
2017/0067019 A1 3/2017 Ho
2017/0073625 A1 3/2017 Kasuto et al.
2017/0226455 A1 8/2017 Fang et al.
2017/0267959 A1 9/2017 Martin et al.
2017/0283757 A1 10/2017 Carter et al.
2017/0306281 A1 10/2017 Martin et al.
2017/0342363 A1 11/2017 Fang et al.
2018/0127698 A1* 5/2018 Niggemann ........... C12M 23/12
2018/0166743 A1 6/2018 Lee et al.
2018/0201888 A1 7/2018 Miwa et al.
2018/0301754 A1 10/2018 Badding et al.
2019/0006707 A1 1/2019 Sakamoto et al.
2020/0064197 A1 2/2020 Furnas
2020/0131461 A1 4/2020 Martin et al.
2020/0181552 A1 6/2020 Martin et al.
2020/0199006 A1 6/2020 Jain et al.
2020/0239854 A1 7/2020 Ayano et al.
2021/0062126 A1 3/2021 Martin et al.
2022/0220434 A1 7/2022 Martin et al.
2022/0259540 A1 8/2022 Li et al.

FOREIGN PATENT DOCUMENTS

CA 2679011 A1 9/2008
CA 2848875 A1 3/2013
CN 2186755 Y 1/1995
CN 1168921 A 12/1997
CN 1234112 A 11/1999
CN 1867663 A 11/2006
CN 1875093 A 12/2006
CN 201261785 Y 6/2009
CN 201626959 U 11/2010
CN 101978041 A 2/2011
CN 102105578 A 6/2011
CN 102257123 A 11/2011
CN 102449135 A 5/2012
CN 102687023 A 9/2012
CN 202450098 U 9/2012
CN 202849407 U 4/2013
CN 103080294 A 5/2013
CN 103119151 A 5/2013
CN 203513696 U 4/2014
CN 103814125 A 5/2014
CN 204608026 U 9/2015
CN 204702760 U 10/2015
CN 204714819 U 10/2015
CN 204752742 U 11/2015
CN 204803327 U 11/2015
CN 205170866 U 4/2016
CN 205669029 U 11/2016
CN 205839030 U 12/2016
CN 205990396 U 3/2017
CN 107109340 A 8/2017
CN 107109341 A 8/2017
CN 107208025 A 9/2017
CN 107460125 A 12/2017
DE 3116926 A1 11/1982
DE 8309876 U1 12/1983
DE 10019862 A1 11/2001
DE 202006017853 U1 1/2007
DE 102009005526 A1 7/2010
DE 102014214077 A1 1/2016
DE 102014017728 A1 6/2016
DE 102015116732 A1 4/2017
EP 0307048 A2 3/1989
EP 0605527 A1 7/1994
EP 0681846 A2 11/1995
EP 0800571 A2 10/1997
EP 0834552 A1 4/1998
EP 0965633 A1 12/1999
EP 1181349 A1 2/2002
EP 1348533 A2 10/2003
EP 1358937 A1 11/2003
EP 1445022 A2 8/2004
EP 1988152 A1 11/2008
EP 2032262 A2 3/2009
EP 2085463 A1 8/2009
EP 2617807 A1 7/2013
EP 2653531 A1 10/2013
EP 2759592 A1 7/2014
EP 2896684 A1 7/2015
EP 3081627 A1 10/2016
EP 3296018 A1 3/2018
EP 3351615 A1 7/2018
EP 3372666 A1 9/2018
GB 2147100 A 5/1985
JP 03-139350 A 6/1991
JP 06-038734 A 2/1994
JP 06-327462 A 11/1994
JP 09-173049 A 7/1997
JP 09-234811 A 9/1997
JP 10-210866 A 8/1998
JP 10-210966 A 8/1998
JP 2001-106749 A 4/2001

(56) References Cited

FOREIGN PATENT DOCUMENTS

| | | | | |
|---|---|---|---|---|
| JP | 2003-135056 | A | | 5/2003 |
| JP | 2003-180335 | A | | 7/2003 |
| JP | 2004-129558 | A | | 4/2004 |
| JP | 2004-535829 | A | | 12/2004 |
| JP | 2005-080660 | A | | 3/2005 |
| JP | 2006-121991 | A | | 5/2006 |
| JP | 2006-191809 | A | | 7/2006 |
| JP | 2007-510429 | A | | 4/2007 |
| JP | 3139350 | U | | 2/2008 |
| JP | 2009-017810 | A | | 1/2009 |
| JP | 2009-050194 | A | | 3/2009 |
| JP | 2009-183288 | A | | 8/2009 |
| JP | 2009-542230 | A | | 12/2009 |
| JP | 2010-088347 | A | | 4/2010 |
| JP | 2010-104327 | A | | 5/2010 |
| JP | 2010-518879 | A | | 6/2010 |
| JP | 2010-158214 | A | | 7/2010 |
| JP | 2011-509686 | A | | 3/2011 |
| JP | 2011-521642 | A | | 7/2011 |
| JP | 2011-172533 | A | | 9/2011 |
| JP | 2011-528226 | A | | 11/2011 |
| JP | 2012-249547 | A | | 12/2012 |
| JP | 2013-055911 | A | | 3/2013 |
| JP | 2014-132869 | A | | 7/2014 |
| JP | 2015-012827 | A | | 1/2015 |
| JP | 2015-029431 | A | | 2/2015 |
| JP | 2015-073520 | A | | 4/2015 |
| JP | 2016-002023 | A | | 1/2016 |
| JP | 5845185 | B2 | | 1/2016 |
| JP | 2016-093149 | A | | 5/2016 |
| JP | 2016-136920 | A | | 8/2016 |
| JP | 2016-136921 | A | | 8/2016 |
| JP | 2017-532970 | A | | 11/2017 |
| JP | 2018108032 | A | * | 7/2018 |
| KR | 10-2014-0113139 | A | | 9/2014 |
| KR | 10-2014-0125662 | A | | 10/2014 |
| KR | 10-2017-0008539 | A | | 1/2017 |
| WO | 92/07063 | A2 | | 4/1992 |
| WO | 93/07258 | A1 | | 4/1993 |
| WO | 96/21851 | A2 | | 7/1996 |
| WO | 98/15355 | A2 | | 4/1998 |
| WO | 98/31466 | A1 | | 7/1998 |
| WO | 01/80997 | A1 | | 11/2001 |
| WO | 01/92462 | A1 | | 12/2001 |
| WO | 2004/044120 | A2 | | 5/2004 |
| WO | 2004/094060 | A1 | | 11/2004 |
| WO | 2005/047464 | A2 | | 5/2005 |
| WO | 2006/043267 | A1 | | 4/2006 |
| WO | 2007/015770 | A1 | | 2/2007 |
| WO | 2007/097120 | A1 | | 8/2007 |
| WO | 2008/006104 | A2 | | 1/2008 |
| WO | 2008/008149 | A2 | | 1/2008 |
| WO | 2008/106771 | A1 | | 9/2008 |
| WO | 2008/118500 | A1 | | 10/2008 |
| WO | 2008/140295 | A1 | | 11/2008 |
| WO | 2008/149039 | A2 | | 12/2008 |
| WO | 2008/153783 | A1 | | 12/2008 |
| WO | 2009/094125 | A2 | | 7/2009 |
| WO | 2009/148509 | A1 | | 12/2009 |
| WO | 2009/148512 | A2 | | 12/2009 |
| WO | 2010/008566 | A2 | | 1/2010 |
| WO | 2010/042072 | A1 | | 4/2010 |
| WO | 2010/069589 | A1 | | 6/2010 |
| WO | 2012/036011 | A1 | | 3/2012 |
| WO | 2012/077683 | A1 | | 6/2012 |
| WO | 2012/170232 | A1 | | 12/2012 |
| WO | 2013/042360 | A1 | | 3/2013 |
| WO | 2013/108293 | A1 | | 7/2013 |
| WO | 2013/116449 | A1 | | 8/2013 |
| WO | 2014/042162 | A1 | | 3/2014 |
| WO | 2014/072432 | A1 | | 5/2014 |
| WO | 2014/140181 | A1 | | 9/2014 |
| WO | 2014/156455 | A1 | | 10/2014 |
| WO | 2014/165273 | A1 | | 10/2014 |
| WO | 2014/171782 | A1 | | 10/2014 |
| WO | 2014/179196 | A1 | | 11/2014 |
| WO | 2014/196204 | A1 | | 12/2014 |
| WO | 2015/033507 | A1 | | 3/2015 |
| WO | 2015/061907 | A1 | | 5/2015 |
| WO | 2015/087369 | A1 | | 6/2015 |
| WO | 2016/020992 | A1 | | 2/2016 |
| WO | 2016/064757 | A1 | | 4/2016 |
| WO | 2016/069885 | A1 | | 5/2016 |
| WO | 2016/069892 | A1 | | 5/2016 |
| WO | 2016/069895 | A1 | | 5/2016 |
| WO | 2016/069917 | A1 | | 5/2016 |
| WO | 2016/069930 | A1 | | 5/2016 |
| WO | 2016/157322 | A1 | | 10/2016 |
| WO | 2017/025584 | A1 | | 2/2017 |
| WO | 2017/047735 | A1 | | 3/2017 |
| WO | 2017/077163 | A1 | | 5/2017 |
| WO | 2017/142410 | A1 | | 8/2017 |
| WO | 2018/068034 | A1 | | 4/2018 |
| WO | 2018/200893 | A1 | | 11/2018 |
| WO | 2019/010401 | A1 | | 1/2019 |
| WO | 2019/014621 | A1 | | 1/2019 |
| WO | 2019/014627 | A1 | | 1/2019 |
| WO | 2019/014635 | A1 | | 1/2019 |
| WO | 2019/014636 | A1 | | 1/2019 |
| WO | 2019/178039 | A1 | | 9/2019 |

OTHER PUBLICATIONS

Wikipedia, “Antiroll Tanks”; 3 Pages; Page Last Edited May 23, 2019.

Wrighton et al, “Forces of Change: Mechanics Underlying Formation of Functional 3D Organ Buds” Cell Stem Cell, May 7, 2015; 16(5): 453-454.

Xu et al, “Characterisation of some cytotoxic endpoints using rat liver and HepG2 spheroids as in vitro models and their application in hepatotoxicity studies. I. Glucose metabolism and enzyme release as cytotoxic markers.” Toxicol Appl Pharmacol 2003;189:100-111.

Yamada et al, “Efficient induction of hepatocyte spheroids in a suspension culture using a water-soluble synthetic polymer as an artificial matrix.” J Biochem 1998; 123:1017-1023.

Yang et al., “An Agarose-Gel Based Method for Transporting Cell Lines”, Current Chemical Genomics, vol. 3, Jan. 2009, pp. 50-53.

Zuidema et al., “Fabrication And Characterization Of Tunable Polysaccharide Hydrogel Blends For Neural Repair”, Acta Biomaterialia, vol. 7, No. 4, Apr. 2011, pp. 1634-1643.

“Identification grid for microplates”, Rtreived from: https://www.kisker-biotech.com/frontoffice/product?produitld=0N-27-11, 2 pAGES, 2021.

“Laboratory Flasks Selection Guide: Types, Features, Applications”, Engineering360, <https://www.globalspec.com/learnmore/labware_scientific_instruments/labware_consumables/laboratory_flasks#:~:text=Laboratory%20flasks%20are%20lab%20vessels, the%20opening%20at%20the%20neck.> accessed Apr. 8, 2022 (Year: 2022).

Achilli et al., “Advances In The Formation, Use And Understanding Of Multi-cellular Spheroids”, Expert Opinion On Biological Therapy, vol. 12, No. 10, Jul. 2012, pp. 1347-1360.

Alepee et al, “State-Of-The-Art 3D Cultures (Organs-On-A-Chip) in Safety Testing and Pathophysiology”; Transatlantic Think Tank for Toxicology, T4 Workshop Report, Altex 31, Apr. 2014, pp. 441-477, Retrieved From: http://dx.doi.org/10.14573/altex1406111 (Jul. 14, 2014).

Aline, “We Engineer Microfluidic Products” ; 7 Pages; (2020) https://alineinc.com/.

Anada et al; “An Oxygen-Permeable Spheroid Culture System for the Prevention of Central Hypoxia and Necrosis of Spheroids”; Biomaterials, 33, (2012) 8430-8441.

AxoSIM, Nerve-on-a-Chip Mini-Brain About Team; 6 Pages; (Downloaded Mar. 9, 2020); http://axosim.com/.

AxoSIM, NerveSim BrianSim About Resources; Available on (http://axosim.com/), Accessed May 13, 2021, 6 Pages.

Bartosh et al; “Aggregation of Human Mesenchymal Stromal Cells (MSCS) Into 3D Spheroid Enhances Their AntiInflammatory Properties”; PNAS, Aug. 3, 2010, vol. 107, No. 31 pp. 13724-13729.

(56) References Cited

OTHER PUBLICATIONS

Bioivt Elevating Science(Registered); 6 Paes; (2020); http://www.hepregen.com/.
Bioivt Elevating Science, Hepatopac® Technology, Available at (https://bioivt.com/about/technologies/hepatopactechnology), Accessed May 13, 2021, 3 Pages.
Brandrup et al., "Polymer Handbook", Fourth Edition, Wiley-Interscience Publication, , Permeability and diffusion data, 1999, 9 pages (Contributors; Preface).
Carver et al.; Multicellular Tumor Spheroids as a Model for Assessing Delivery of Oligonucleotides in Three Dimensions; Molecular Therapy-Nucleic Acids (2014) 3, E153; 8 Pages.
Chen et al, "Microfluidic array for three-dimensional perfusion culture of human mammary epithelial cells." Biomed Microdevices, vol. 13 (2011), pp. 753-758.
Cheng et al, "MicroRNA-34a Targets Forkhead Box J2 to Modulate Differentiation of Endothelial Progenitor Cells in Response to Shear Stress", J Mol Cell Cardiol. 74 (2014) 4-12.
Choi et al., "Feasibility of a simple double-layered coculture system incorporating metabolic processes of the intestine and liver tissue: application to the analysis of benzo[a]pyrene toxicity" Toxicology in Vitro, vol. 18, pp. 393-402, 2004.
CN-Bio, "Transforming Drug Discovery and the Lives of Patients"; 5 Pages; (2020) http://cn-bio.com/.
Colazzo et al, "Shear Stress and VEGR Enhance Endothelial Differentiation of Human Adipose-Derived Stem Cells", Growth Factors, 2014, 32(5):139-149.
Corning Life Sciences Product Portfolio; 5 Pages Saved Mar. 6, 2020.
Corning(Registered) HTS TRANSWELL(Registered)-96 Tissue Culture Systems, Permeable Supports for High Throughput Screening Applications; 2 Pages (2004).
Curcio et al. "Mass transfer and metabolic reactions in hepatocyte spheroids cultured in rotating wall gas-permeable membrane system." Biomaterials 28 (2007) 5487-5497. (Year: 2007).
Dolznig et al, "Organotypic spheroid cultures to study tumor-stroma interaction during cancer development", Drug Discovery Today: Disease Models, 2011, 8(2-3):113-118.
Domansky et al, "Perfused Multiwell Plate For 30 Liver Tissue Engineering", Lab Chip, 2010, 10:51-58.
Elveflow; "Microfluidics Innovation Center"; 6 Pages; (Downloaded Mar. 9, 2020); https://www.elveflow.com.
Emulate, 6 Pages; (2019) https://emulatebio.com/.
Endo et al., "Gene transfection to spheroid culture system on micropattemed culture plate by polyplex nanomicelle: a novel platform of genetically-modified cell transplantation", Drug Deliv. and Transl. Res., 2012, vol. 2, p. 398-405.
Engelberg et al., "Essential operating principles for tumor spheroid growth", BMC Systems Biology 2008, 2:110, 19 pages.
Evenou et al. "Spontaneous Formation of Highly Functional Three-Dimensional Multilayer from Human Hepatoma Hep G2 Cells Cultured on an Oxygen-Permeable Polydimethylsiloxane Membrane." Tissue Engineering: Part C vol. 16, No. 2, 2010, pp. 311-318. (Year: 2010).
Friedrich et al. "Spheroid-based drug screen: considerations and practical approach." Nature protocols, 2009, vol. 4 No. 3, 309-323.
Friedrich et al: "Experimental anti-tumor therapy in 3-D: spheroids-old hat or new challenge?" Int J Radiat Biol 2007, 83:849-871.
Frith et al. "Dynamic three-dimensional culture methods enhance mesenchymal stem cell properties and increase therapeutic potential." Tissue engineering, 2010, 16, No. 4, 735-749.
Fukuda et al, "Efficacy of a polyurethane foam/spheroid artificial liver by using human hepaloblastoma cell line (Hep G2)", Cell Transplantation, 2003, 12:51-58.
G-Plate: Accelerate your cell cultures to the next dimension, "An original cell culture model allowing for inland shaped 3D cell aggregates" 1 page, retrieved Sep. 8, 2015.
GeoCHEM Incorporated, Product Line; hllps://www.geocheminc.com, 4 Pages; (2020).
HμREL (Registered) Corporation, Bioanalytic Tools Company; 2 Pages; (2013); http://hurelcorp.com/.
Haycock, "3D cell culture: a review of current approaches and techniques", Methods Mol Biol, 2011; 695:1-15.
Hirschhaeuser et al., "Multicellular tumor spheroids: An underestimated tool is catching up again." Journal of Biotechnology, 2010, 148, 3-15.
Howes et al; "3-Dimensional Culture Systems for Anit-Cancer Compound Profiling and High-Throughput Screening Reveal Increases in EGFR Inhibitor-Mediated Cytotoxicity Compared To Monolayer Culture Systems"; PLOS One; Sep. 2004, vol. 9, Issue 9, 11 Pages.
Hribar et al; "Nonlinear 3D Projection Printing of Concave Hydrogel Microstructures for Long-Term Multicellular Spheroid and Embryoid Body Culture"; Lab Chip, 2015, 15, 2412-2418.
Hsiao et al., "Effects of 3D Microwell Culture on Initial Fate Specification in Human Embryonic Stem Cells", Published in final edited form as AlChE J. vol. 60 No. 4, Apr. 2014, pp. 1225-1235.
Huang et al., "Preparation of dense Ta-LLZO/MgO composite Li-ion solid electrolyte: Sintering, microstructure, performance and the role of MgO", Journal of Energy Chemistry, vol. 39, 2019, pp. 8-16.
Hwang et al; "Microwell-Mediated Control of Embryoid Body Size Regulates Embryonic Stem Cell Fate via Differential Expression of WNT5A and WNT11"; PNAS; Oct. 6, 2009, vol. 106, No. 40, pp. 16978-16983.
Jeon et al, "Combined Effects of Flow-Induced Shear Stress and Micropatterned Surface Morphology on Neuronal Differentiation of Human Mesenchymal Stem Cells" J Biosci Bioeng, 2014, 117(2):242-247.
Jiang et al, "Shear Enhances Thrombopoiesis and Formation of Microparticles That Induce Megakaryocytic Differentiation of Stem Cells", Blood, Sep. 25, 2014; 124(13):2094-2103.
Junji Fukuda et al., "Hepatocyte Spheroid Arrays Inside Microwells Connected With Microchannels", Biomicrofluidics 5, 2011, p. 10.
Kelm et al, "Method for generation of homogeneous multicellular tumor spheroids applicable to a wide variety of cell types", Biotechnology and Bioengineering 2003; 83(2):173-180.
Kim et al, "Shear Stress Induced by an Interstitial Level of Slow Flow Increases the Osteogenic Differentiation of Mesenchymal Stem Cells Through Taz Activation" PLoS ONE, Mar. 21, 2014; 9(3), e92427, 9 pages.
Koide et al, "Formation of multicellular spheroids composed of adult rat hepatocytes in dishes with positively charged surfaces and under other nonadherent environments", Exp Cell Res 1990; 186:227-235.
Koike et al. "Characterization of Embryo id Bodies of Mouse Embryonic Stem Cells Formed under Various Culture Conditions and Estimation of Differentiation Status of Such Bodies." Journal of Bioscience and Bioengineering vol. I 04, No. 4, 294-299. 2007. (Year: 2007).
Kunz-Schughart et al, "The use of 3-D cultures for high-throughput screening: the multicellular spheroid model", J Biomol Screen 2004, 9(4):273-285.
Kutsuzawa et al, "Highly Robust Protein Production vy Co-Culture of CHO Spheroids Layered on Feeder Cells in Serum-Free Medium"; Colloid Polym Sci (2014) 292; 839-848.
Labusca et al. "Scaffold-free culture of mesenchymal stem cell spheroids in suspension preserves multilineage potential", Cell Tissue Res. Mar. 2012; 347(3):701-711.
Labusca, "Scaffold free 3D culture of mesenchymal stem cells; implications for regenerative medicine", J Transplant Stem Cel Biol 2015 2(1): 8.
Landry et al, "Spheroidal aggregate culture of rat liver cells: histotypic reorganization, biomatrix deposition, and maintenance of functional activities" J Cell Biol 1985; 101:914-923.
Lau et al., "Evaluation of a Novel in Vitro CACO-2 Hepatocyte Hybrid System for Predicting in Vivo Oral Bioavailability" Drug Metabolism and Disposition, vol. 32, No. 9, pp. 937-942, 2004.
Lin et al., "La2Zr2O7 and MgO co-doped composite Li-Garnet solid electrolyte", Journal of Energy Chemistry, vol. 40, 2020, pp. 132-136.
Liquid Surge Control, LLC; "The Latest in Drop-In Baffle Technology"; 2 Pages; (2019).

(56) References Cited

OTHER PUBLICATIONS

Liu et al. "Quasi-spherical microwells on superhydrophobic substrates for long term culture of multicellular spheroids and high throughput assays" Biomaterials and Cancer 35 (2014) pp. 6060-6068.
Liu et al; "Advanced Micromachining of Concave Microwells for Long Term On-Chip Culture of Multicellular Tumour Spheroids", ACS Appl. Mater. Interfaces, 2014, 35 Pages.
Lonza Inc., "SeaPrep Agarose: An Ultralow Gelling, Soft Agarose", Available Online at <http://www.lonzabio.jp/catalog/pdf/pd/PD031.pdf>, 2007, pp. 1-4.
Lovett et al. "Vascularization Strategies for Tissue Engineering" Tissue Engineering Part B, 2009, vol. 15, No. 3, pp. 353-370.
Lquid Surge Control, LLC; "The Latest in Drop-In Baffle Technology"; 2 Pages; (2019).
Lu et al. "Galactosylated PVDF membrane promotes hepatocyte attachment and functional maintenance." Biomaterials 2003;24:4893-903.
Markovitz-Bishitz, "A polymer microstructure array for the formation, culturing, and high throughput drug screening of breast cancer spheroids" Biomaterials and Biotechnology 31 (2010) pp. 8436-8444.
Martin et al., "Agarose And Methylcellulose Hydrogel Blends For Nerve Regeneration Applications", J. Neural Eng., vol. 5, 2008, pp. 221-231.
McMillan, "Shear stress in microfluidic devices" Darwin Microfludics interner article (Year: 2017).
Messner et al, Multi-cell type human liver microtissues for hepatotoxicity testing. Archives of Toxicology, Nov. 11, 2012, 5 pages.
Mimetas the Organ-on-a-Chip Company; "Organ-on-a-Chip Models for Science and Pharma"; 4 Pages; (Downloaded Mar. 9, 2020); https://mimetas.com/.
Mironov et al; "Organ Printing: Tissue Spheroids as Buliding Blocks" Biomaterials, 2009; 30 (12) 2164-2174.
Moon et al; "Optimizing Human Embryonic Stem Cells Differentiation Efficiency by Screening Size-Tunable Homogenous Embryoid Bodies"; Biomaterials; 35 (2014) 5987-5997.
Murphy et al; "3D Bioprinting of Tissues and Organs"; Nature Biotechnology, vol. 32, No. 8. Aug. 2014, pp. 773-785.
Nortis; "Bridging the Gap Between in Vitro and in Vivo Research"; 16 Pages; (2015); https://www.nortisbio.com/.
Organovo, "Pioneering Bioprinted Tissues To Treat Disease"; 2 Pages; (Downloaded Mar. 9, 2020) http://organovo.com/.
Otsuka et al, "Two-dimensional multiarray formation of hepatocyte spheroids on a microfabricated PEG-brush surface." ChemBioChem 2004; 5:850-855.
Peshwa et al., "Mechanistics of formation and ultrastructural evaluation of hepatocyte spheroids." In Vitro Cell Dev Biol Anim 1996; 32:197-203.
Polyimide: Japan Polyimide and Aromatic Polymers Study Group, 2010, pp. 364-371 Table 2.
Rezende et al, "Scalable Biofabrication of Tissue Spheroids for Organ Printing"; Sciverse Science Direct, Procedia CIRP 5, (2013) 276-281.
Sa et al. "Round-bottomed Honeycomb Microwells: Embryoid body shape correlates with stem cell fate" Journal of Developmental Biology and Tissue Engineering vol. 4(2), pp. 12-22, May 2012.
Sakai et al, "Detachably Assembled Microfluidic Device for Perfusion Culture and Post-Culture Analysis of Spheroid Array"; Biotechnol. J. 2014, 9, 971-979.
Sakai et al, "Large-scale preparation and function of porcine hepatocyte spheroids." Int J Artif Organs 1996; vol. 19, No. 5, pp. 294-301.
Sakai et al, "Technique for the Control of Spheroid Diameter Using Microfabricated Chips"; Sciencedirect, Acta Biomaterialia 3 (2007) 1033-1040.
Sakai et al; "Technique for the Control of Spheroid Diameter Using Microfabricated Chips"; Sciencedirect, Acta Biomaterials 3 (2007) 1033-1040.
Sart et al. "Three-dimensional aggregates of mesenchymal stem cells: cellular mechanisms, biological properties and applications." Tissue engineering, 2013, Part B, vol. 20, No. 5, pp. 1-16.
Satoh et al, "A Pneumatic Pressure-Driven Multi-Throughput Microfluidic Circulation Culture System" Lab Chip, 2016, 16, 2339-2348.
Seldon et al; "Evaluation of Encapsulated Liver Cell Spheroids in a Fluidised-Bed Bioartificial Liver for Treatment of Ischaemic Acute Liver Failure in Pigs in the Translational Setting": PLOS One; Dec. 2013, vol. 8, Issue 12, 12 Pages.
Stemcell Technologies, Reproducible and Uniform Embryoid Bodies Using AggreWell Plates, StemCell Technologies, Version 3.0.0, Mar. 2011, Catalog #29146, pp1-28.
Takezawa et al. "Morphological and immunocytochemical characterization of a heterospheroid composed of fibroblasts and hepatocytes." J Cell Sci 1992; 101:495-501.
Tara; "Innovating Predictive Cardiac Physiology"; 4 Pages; (2019) http://tarabiosystems.com/.
The Lab Depot(Registered) Products for Discovery Lab Supplies; Shake Flasks, 3 And 4 Baffles Product Information; 5 Pages (2019).
Tissue Dynamics, "Disruptive Drug Development"; 3 Pages; (Downloaded Mar. 9, 2020); https://www.tissuedynamics.com/.
Tissuse, "Emulating Human Biology, Pioneering Human-on-a-Chip Developments"; 1 Page; (Downloaded Mar. 9, 2020) https://www.tissuse.com/en/.
Tissuse; Technology, Available on (https://www.tissuse.com/en/technology/), Accessed May 11, 2021, 4 pages.
Tobe et al, "Receptor-mediated formation of multilayer aggregates of primary cultured adult rat hepatocytes on tactose-subsliluled polystyrene" Biochem Biophys Res Commun 1992; 184(1):225-230.
Tong et al, "Long-term culture of adult rat hepatocyte spheroids." Exp Cell Res 1992; 200:326-332.
TPP, webpage entitled "Tissue Culture Flask with re-closable Lid", <http://www.Istbio.com/shop/goods/goods_view.php?goodsno=15> cached by Internet Archive Apr. 8, 2017, screenshot attached (Year: 2017).
Truckemller, et al., Thermoforming of Film-Based Biomedical Microdevices, Adv. Mater. 2011, 23, pp. 1311-1329.
Tung et al, "High-throughput 3D spheroid culture and drug testing using 384 hanging drop array" Analyst, 2011, 136 (3), 473-478.
Uchida et al; "An Injectable Spheroid System With Genetic Modification for Cell Transplantation Therapy"; Biomaterials, 35 (2014) 2499-2506.
Urich et al, "Multicellular Self-Assembled Spheroidal Model of the Blood Brain Barrier"; Scientific Reports, 3, 1500, 8 Pages.
Vinci et al. Advances in establishment and analysis of three-dimensional tumor spheroid-based functional assays for target validation and drug evaluation, BMC Biology 2012, 10:29.

* cited by examiner

MICROCAVITY PLATE

CROSS-REFERENCE TO RELATED APPLICATIONS

This is a national stage application under 35 U.S.C. § 371 of International Application No. PCT/US2021/056736, filed Oct. 27, 2021, which claims the benefit of priority under 35 U.S.C. § 119 of U.S. Provisional Application Ser. No. 63/107,663 filed on Oct. 30, 2020, the content of which is relied upon and incorporated herein by reference in its entirety.

TECHNICAL FIELD

This disclosure generally relates to microcavity plates. In particular, the present disclosure relates to microcavity plates for use in cell culture and high throughput screening.

BACKGROUND

Drug discovery and development is a first step in the process for finding treatment methods for many diseases. That step includes testing many molecular compounds as potential candidates for medical treatment. Due to the amount of testing, high throughput screening (HTS) is often used to conduct the testing. HTS uses automated equipment to rapidly test biological activity of numerous samples. Microplates are often used for HTS, and a 1536-well plate is a typical configuration of microplate for which there is automated handling.

In order to more accurately represent the environment experienced by cells in vivo, 3D cell culture models or spheroids may be used in HTS. The spheroids or 3D cell cultures generally have diameters in the range of about 100-300 microns. Conventional technologies may allow spheroids to be dispensed in 96-well or 384-well plates. However, due to the size of the spheroids, the well geometry in 1536-well plates may not allow for dispensing spheroids into wells of a 1536-well plate. Therefore, conventional 1536-well cell culture devices for generating 3D cell cultures or spheroids typically do not lend themselves to automated handling in HTS processes. Furthermore, there is a lack of conventional equipment available to dispense large structures such as spheroids cultured in a bulk spheroid production vessel into 1536-well plates for HTS.

SUMMARY

Embodiments of the disclosure provide a microcavity plate for bulk spheroid production that may also be used in HTS processes. The microcavity plate comprises 1536 shallow cavities with each cavity having a 1500 μm diameter. The cavities are arranged in the same ordered rows and columns as a typical 1536-well plate. In embodiments, a grid may be added to a top surface of the microcavities to treat each microcavity as an individual to permit HTS. Therefore, embodiments of the disclosure resolve the existing conventional equipment issues, since the spheroids cultured together from the start of the culture process can then be addressed individually after placement of the grid.

In an aspect, a microcavity plate comprises a base comprising: a bottom grid comprising a plurality of grid segments arranged in ordered rows and columns to form a plurality of openings, and an open well comprising a plurality of sidewalls extending vertically from a perimeter of the bottom grid; and a microcavity substrate comprising a plurality of microcavities arranged in ordered rows and columns that align with the plurality of openings in the bottom grid, each microcavity comprising a cavity disposed within an opening of the bottom grid.

In some embodiments, the microcavity plate further comprises an upper grid. In some embodiments, the upper grid comprises a plurality of well openings in ordered rows and columns that mirror the ordered rows and columns of the bottom grid. In some embodiments, the upper grid is configured for placement in the open well on top of the bottom grid delineating the ordered rows and columns of the base. In some embodiments, the plurality of well openings align with the plurality of microcavities in the microcavity substrate. In some embodiments, a microcavity well is defined by sidewalls comprising grid segments that define each microcavity opening, and an individual microcavity centered within the microcavity opening.

In some embodiments, the microcavity plate further comprises a gasket material. In some embodiments, the gasket material is integrated on a bottom of the upper grid, wherein when the upper grid is inserted in the open well, the gasket material is disposed between the bottom of the upper grid and a top of the microcavity substrate.

In some embodiments, the plurality of microcavities comprises 1536 individual microcavities.

In some embodiments, each cavity in the plurality of microcavities comprises a top surface and a rounded bottom. In some embodiments, a diameter of each microcavity at the top surface of the microcavity is about 1500 μm.

In some embodiments, an inner surface of the cavity is coated with a coating non-adherent to cells. In some embodiments, the coating comprises an ultra low attachment (ULA) surface coating.

In some embodiments, the upper grid comprises a plurality of protrusions extending from a perimeter of the upper grid. In some embodiments, protrusions in the plurality of protrusions are configured to align and interlock with a plurality of through holes in the sidewalls of the open well.

In some embodiments, the microcavity substrate is formed from polymers selected from polystyrene, polypropylene, polyethylene, polyethylene terephthalate, polymethylpentene, polycarbonate, polymethyl methacrylate, styrene-butadiene copolymers, styrene-ethylene-butylene-styrene, other such polymers, or a combination thereof. In some embodiments, the microcavity substrate is formed from polystyrene.

In some embodiments, the base is formed from a polymer comprising polystyrene, polypropylene, polyethylene, polyethylene terephthalate, polymethylpentene, polycarbonate, polymethyl methacrylate, styrene-butadiene copolymers, styrene-ethylene-butylene-styrene, other such polymers, or a combination thereof. In some embodiments, the base is formed from polystyrene.

In some embodiments, the upper grid is formed from elastomeric materials selected from natural rubbers, styrene-butadiene block copolymers, styrene-ethylene-butylene-styrene polymers, polyisoprene, polybutadiene, ethylene propylene rubber, ethylene propylene diene rubber, silicone elastomers, fluoroelastomers, polyurethane elastomers, nitrile rubbers, or a combination thereof.

In some embodiments, the gasket material is formed from an elastomer. In some embodiments, the elastomer comprises silicone. In some embodiments, the gasket material is a pressure sensitive adhesive.

In some embodiments, the microcavity plate is used for cell culture of spheroids. In some embodiments, the microcavity plate is used for high-throughput screening.

In an aspect, a method of high-throughput screening comprises seeding cells in a microcavity plate as described herein. The method further comprises culturing the cells to form spheroids within the plurality of microcavities; attaching an upper grid to a top portion of the plurality of microcavities within the microcavity plate to form microcavity wells; and treating each of the microcavity wells as an individual for high throughput screening of the cultured spheroids. In some embodiments, culturing the cells comprises contacting the cells in the microcavity plate with cell culture media.

DETAILED DESCRIPTION

In order to more accurately represent the environment experienced by cells in vivo, 3D cell culture models may be used in HTS. Recent research demonstrates that cell responses in 3D cultures, such as 3D spheroids or organoids (hereafter referred to as spheroids), are more similar to in vivo behavior than the cell responses in two-dimension (2D) cultures where cells are cultured in a monolayer. The additional dimensionality of 3D cultures is believed to lead to the differences in cellular responses because it influences the spatial organization of the cell surface receptors engaged in interactions with surrounding cells and induces physical constraints to cells, thereby affecting the signal transduction from the outside to the inside of cells, ultimately influencing gene expression and cellular behavior. Conventional culture devices for generating 3D cell cultures or spheroids do not optimally lend themselves to automated handling in HTS processes.

Figure 1:
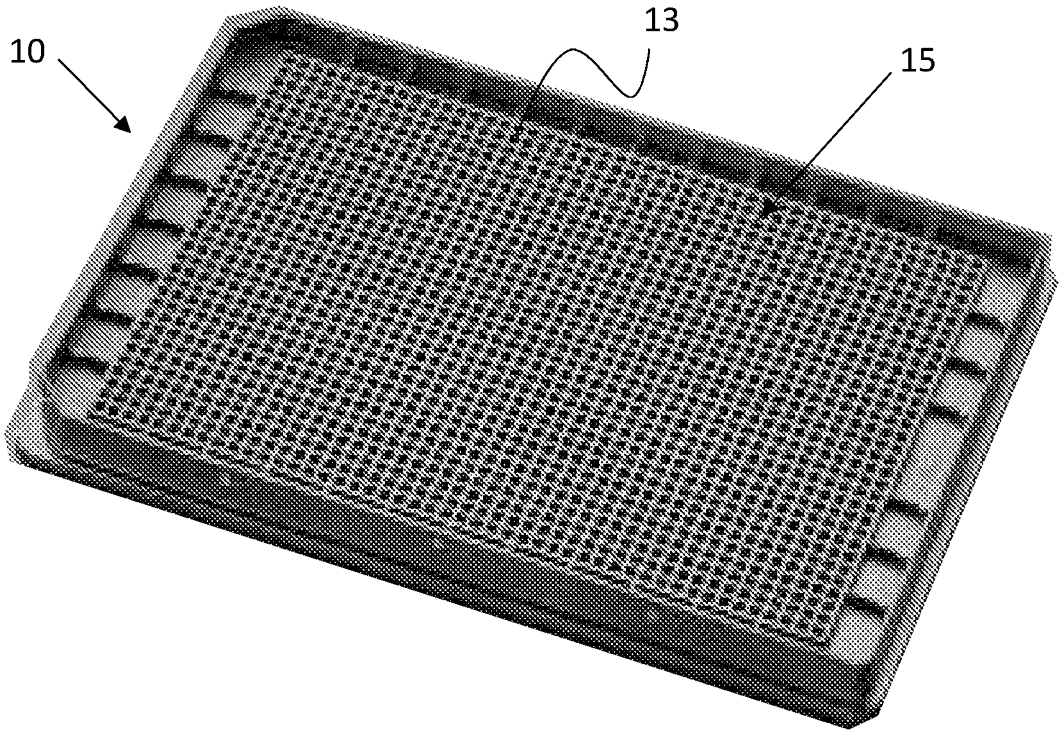
FIG. 1 is an image of a standard 1536-well plate.

Microplates are often used for HTS, and a 1536-well plate is a typical configuration of microplate for which there is automated handling. FIG. 1 is an image of a standard 1536-well plate with regular spacing of individual wells 13 of a plurality of wells 15 arranged in rows and columns. In the microplate, the wells are regularly spaced in rows and columns over a working surface area for a 1536-well plate is about 4.5 inches by about 3 inches. The wells in a 1536-well plate are approximately 1500 μm in diameter and very deep (6000 μm) so that each one of the wells is treated as an individual, making manual handling difficult.

In contrast to microplate wells, which are millimeter (mm) or centimeter (cm)-sized, conventional culture devices for generating 3D cell cultures or spheroids have micron-sized wells. There are several different names for culture devices having wells that are micron-sized, including microcavities and microspaces. Microcavities typically include an inner cavity with a rounded bottom that is non-adherent to cells, and which facilitates 3D cell culture by allowing cells seeded into the microcavities to self-assemble or attach to one another to form a spheroid in each microcavity. Typical microcavities are shallow (~500-3000 μm) and permit cell culture medium to cover all of the spheroids in all cavities at once to make manual handling easy.

Figure 2:
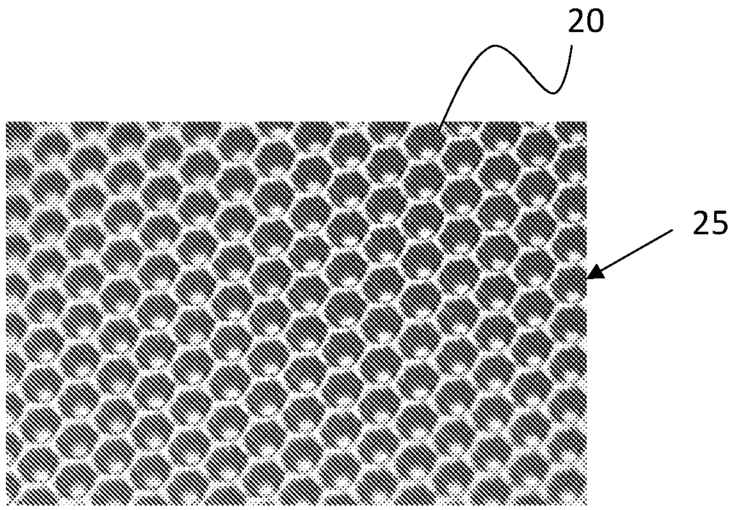
FIG. 2 is an image of microcavities having a hexagonal close-packing configuration.

Microcavity vessels are referred to as bulk spheroid production vessels and can culture many spheroids at once due to the micron-sized geometry of the wells and hexagonal close-packing density or "honeycomb" well configuration. FIG. 2 is an image showing a plurality of microcavities 20 in a hexagonal close-packing configuration 25. Such packing density allows for approximately 12,588 wells that are 500 μm in diameter in a typical microplate working surface area of 4.5 inches×3 inches. If the microcavity diameter is increased to 1500 μm (the diameter of a well in a 1536-well plate), the hexagonal close-packing well density would allow for approximately 2845 wells in a typical microplate working surface area of 4.5 inches×3 inches. Though the hexagonal close-pack configuration of wells allows for bulk spheroid production, conventional bulk spheroid production vessels lack the automated handling configuration of regularly spaced wells in rows and columns and thus cannot be used in standard equipment used for HTS.

Embodiments of the disclosure provide a microcavity plate for bulk spheroid production that may also be used in HTS processes. The microcavity plate comprises 1536 shallow cavities with each cavity having a 1500 μm diameter. The cavities are arranged in the same ordered rows and columns as a typical 1536-well plate. The ordered arrangement of the microcavities in rows and columns allows for an upper grid to be added to a top surface of the microcavities. By adding the upper grid, each microcavity has its own well and can be treated as an individual to permit HTS. Therefore, embodiments of the disclosure allow for spheroids to be cultured together from the start of the culture process to create a homogeneous culture environment, but also allow spheroids to be addressed individually after placement of the grid.

Microcavity plates according to embodiments of the disclosure provide a homogenous culturing environment. Before an upper grid is disposed in the microcavity plate to form individual wells, all spheroids cultured in the 1536-well microcavity plate may receive the same treatment at the same time, thereby providing a homogenous culture environment. In contrast, typical plates with individual wells have more of a heterogenous culture environment because dispensing the same volume to each well is difficult, even with automated equipment.

Microcavity plates according to embodiments described herein may be converted into a plate with individual wells through the addition of an upper grid. The upper grid may be disposed within the plate at a top of the plurality of microcavities. The configuration of a microcavity plate with individual wells will allow for users to perform HTS, as the subsequently added grid will allow the spheroid in each well to be treated separately.

Microcavity plates of embodiments described herein do not require an automated dispenser for handling spheroids or transferring spheroids from a bulk spheroid production vessel to a 1536-well plate.

Figure 3:
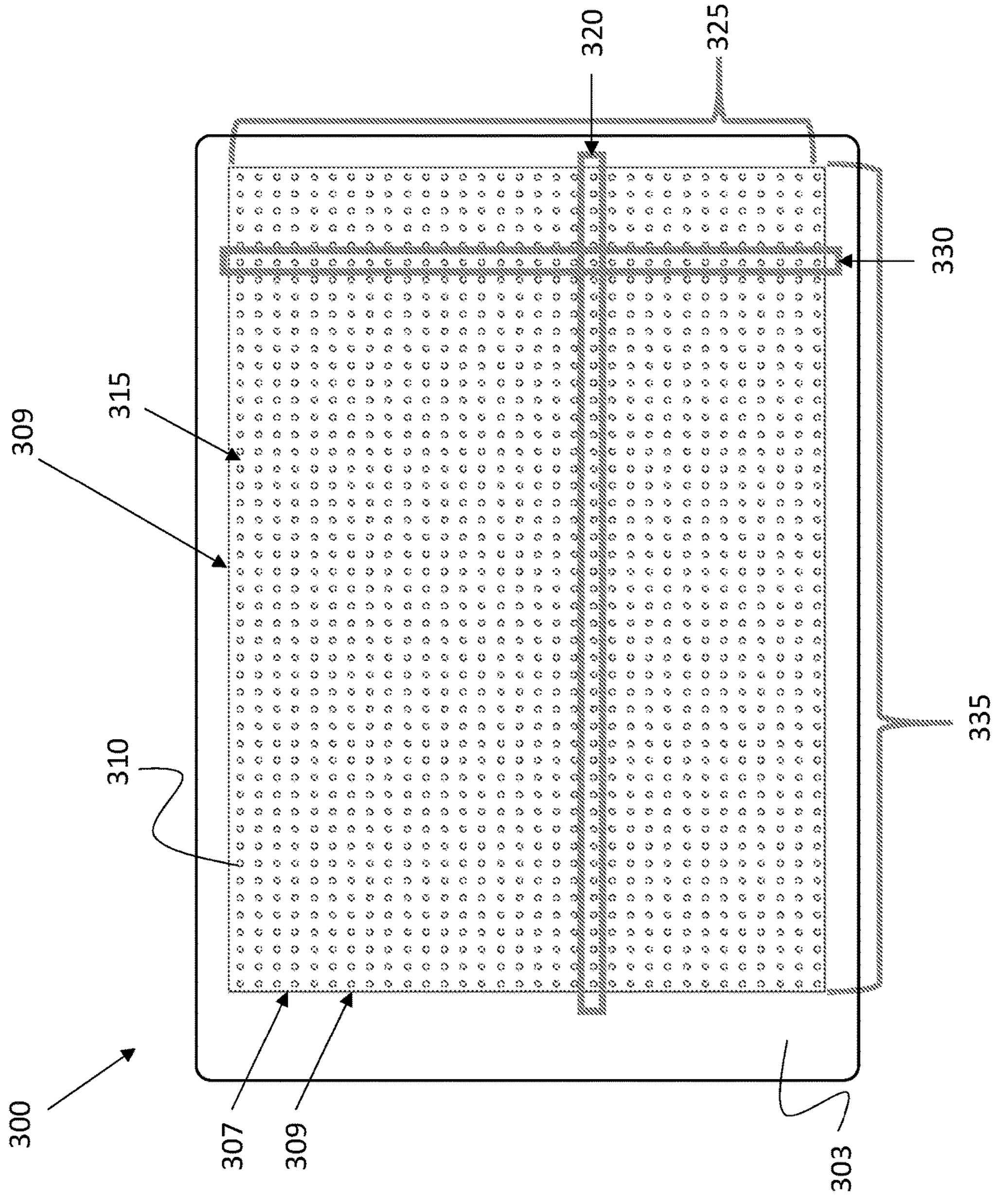
FIG. 3 shows a top view of a 1536 microcavity plate according to an embodiment of the disclosure.

FIG. 3 shows an overhead view of a 1536 microcavity plate without the upper grid in place. The microcavity plate 300 comprises a base 303 of the plate. The base 303 has an open well 307 disposed thereon, the rectangular open well 307 defined by four sidewalls 309 that extend vertically from the base 303. A plurality of microcavities 315 are disposed within the open well 307. Each microcavity 310 is a shallow cavity having a diameter of about 1500 um. The plurality of microcavities 315 are ordered in a plurality of rows 325 and a plurality of columns 335. Each row 320 is parallel to the other rows in the plurality of rows 325. Similarly, each column 330 is parallel to other columns in the plurality of columns 335. In a 1536 microcavity plate, each row 320 comprises 48 microcavities spaced equally apart from one another in a first direction, and each column 330 comprises 32 microcavities spaced equally apart from one another in a second direction. The second direction is perpendicular to the first direction which form a grid pattern from the plurality of rows 325 and the plurality of columns 335.

Figure 4:
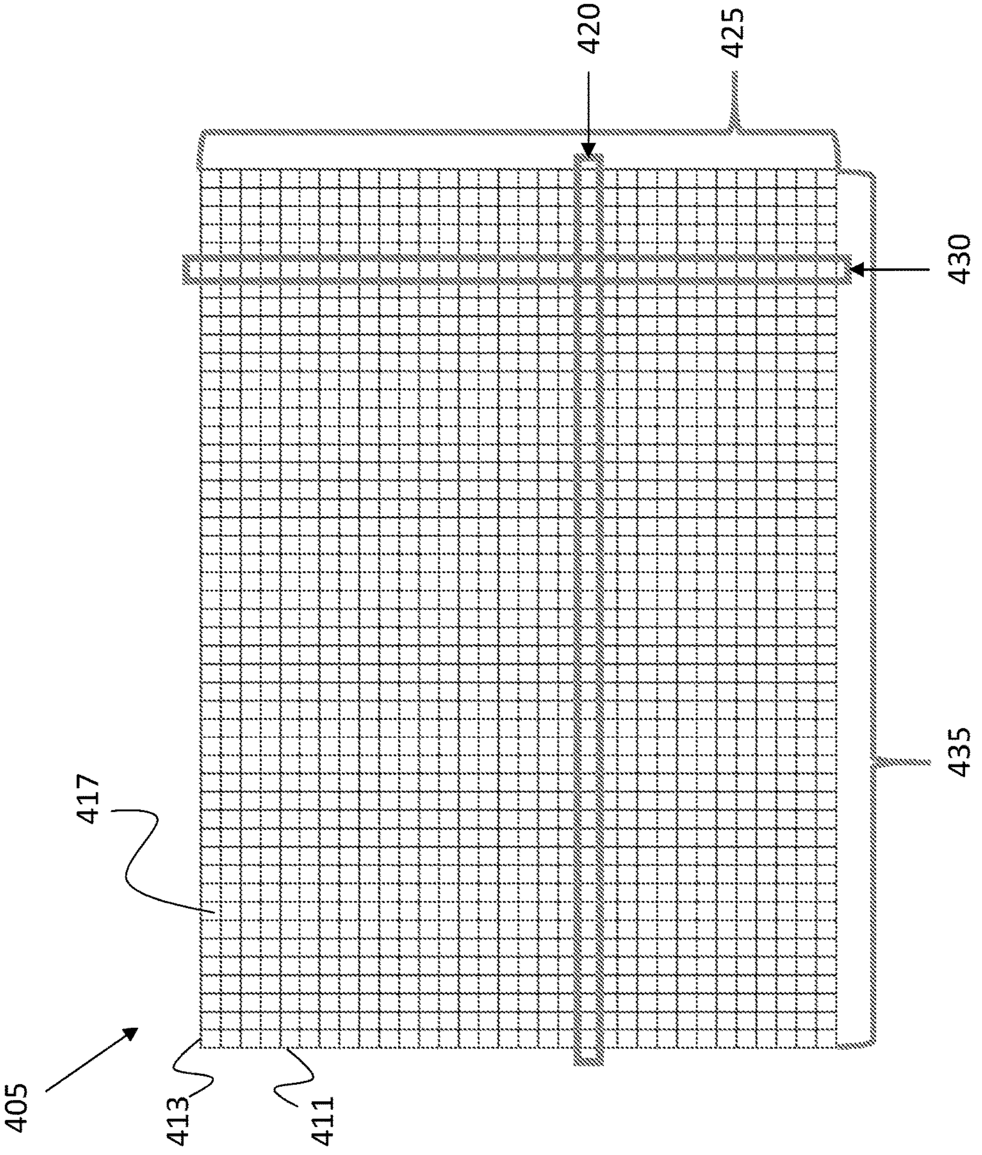
FIG. 4 shows a top view of a grid for use with a 1536 microcavity plate according to an embodiment of the disclosure.

FIG. 4 shows an overhead view of upper grid used for placement in a 1536 microcavity plate. The upper grid 405 is rectangularly shaped to be disposed within the four sidewalls of the open well of the microcavity plate. The upper grid 405 comprises a plurality of grid segments in a first direction 411 and a plurality of grid segments in a second direction 413. The grid segments in the first direction 411 are arranged perpendicular to the grid segments in the second direction 413 to form a grid pattern. The grid segments form a plurality of openings in the grid in ordered rows 425 and columns 435. Each row 420 comprises 48 openings that are equally spaced apart, and each column 430 comprises 32 openings that are equally spaced apart. The upper grid 405 is sized to have openings 417 which frame an individual microcavity in a microcavity plate. When the grid is disposed in place on the microcavity plate, a plurality of individual microcavity wells are formed, wherein the upper grid forms the sidewalls of each microcavity well.

Figure 5:
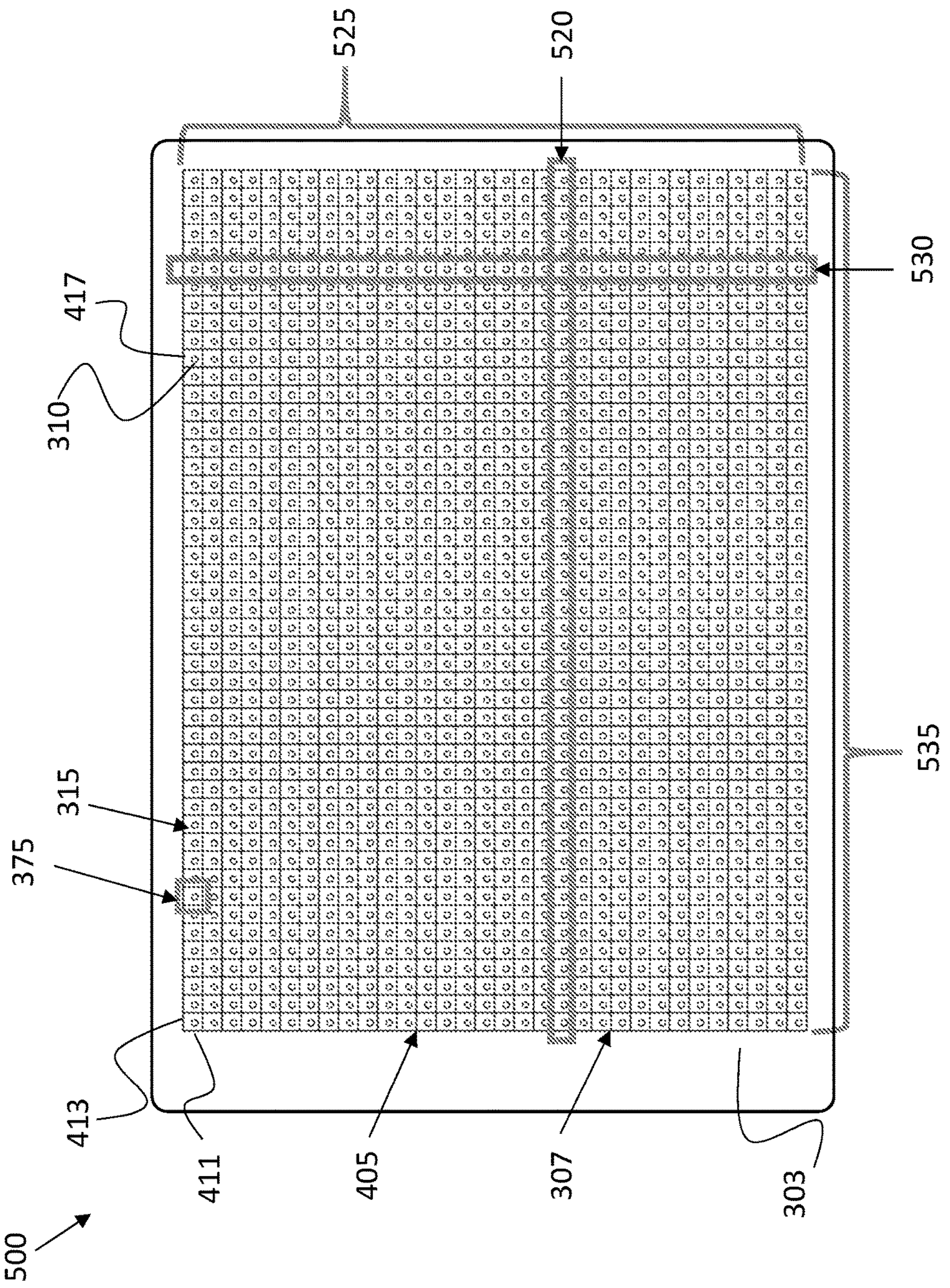
FIG. 5 shows a top view of a 1536 microcavity plate with grid according to an embodiment of the disclosure.

FIG. 5 shows an overhead view of a 1536 microcavity plate with the upper grid in place. The 1536 microcavity plate with upper grid device 500 shown in FIG. 5 comprises 1536 individual microcavity wells 375. The individual microcavity wells 375 are ordered in a plurality of columns 535 and a plurality of rows 525. Each column of microcavity wells 530 comprises 32 microcavity wells. Each row of microcavity wells 520 comprises 48 microcavity wells.

Figure 6:
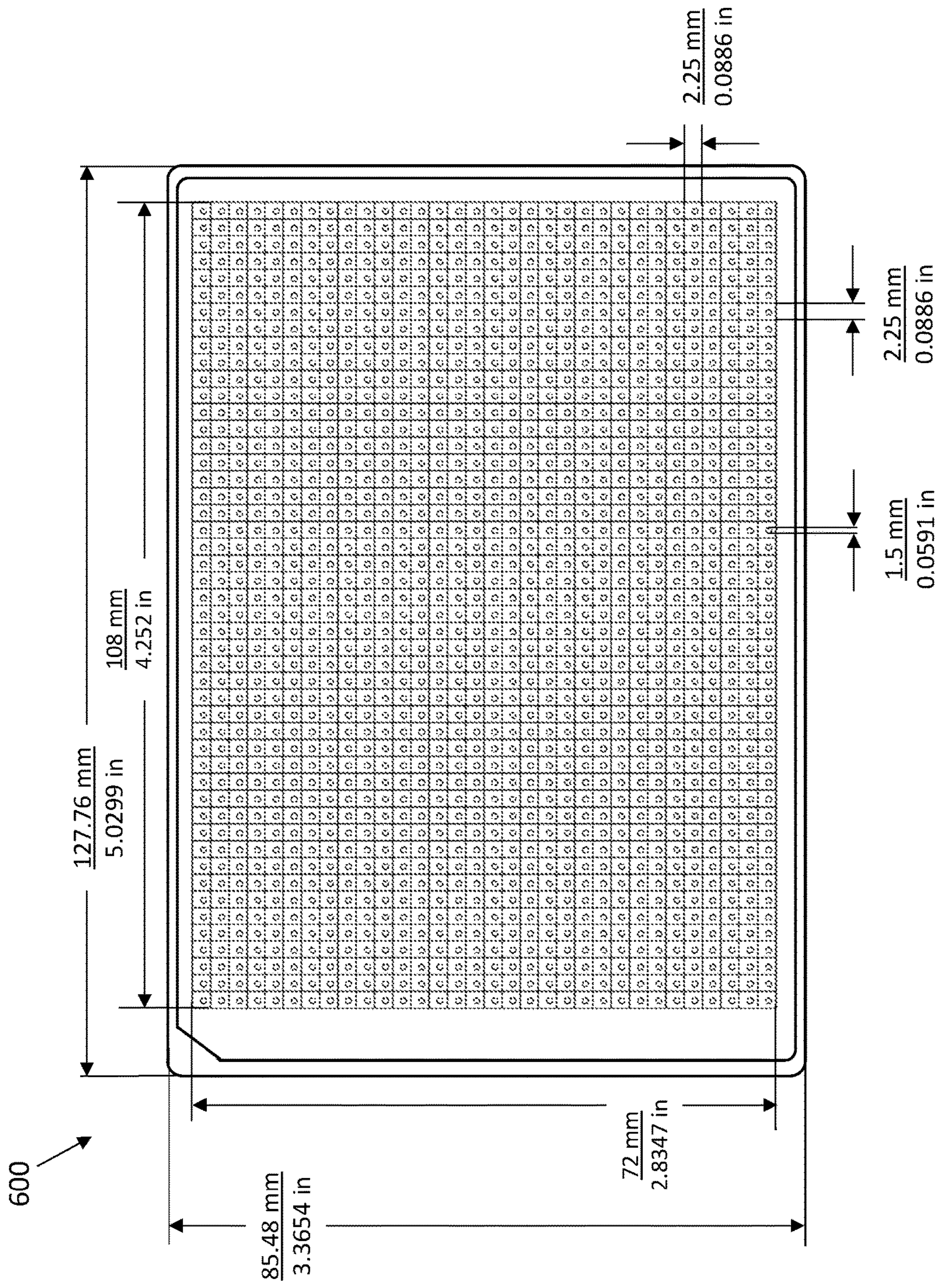
FIG. 6 shows a top view of a 1536 microcavity plate with grid according to an embodiment of the disclosure.

FIG. 6 shows an overhead view of an embodiment of a 1536 microcavity plate 600 with the upper grid in place. FIG. 6 shows an embodiment of a 1536 microcavity plate 600 with dimensions provided as a nonlimiting example of dimensions that may be used for a 1536 microcavity plate described herein. Microcavity plates according to embodiments described herein may comprise a footprint having dimensions standard to a conventional 1536 well plate, such as standard footprint dimensions for microplates defined by the American National Standards Institute (ANSI) and Society for Biomolecular Sciences (SBS) for 1536 well plates. For example, in some embodiments, a length of the microcavity plate is about 5.0299 inches. In some embodiments, a width of the microcavity plate is about 3.3654 inches. In some embodiments, the working area of the microcavity plate is defined by the open well area, which has a length of about 4.252 inches and a width of about 2.8347 inches. In embodiments, each microcavity well has a length of about 0.0886 inches and a width of about 0.0886 inches, with an individual microcavity centered in each microcavity well. In embodiments, each microcavity has a diameter of about 1500 μm (0.05906 inches). In embodiments, a height of the microcavity plate is about 0.780 inches, compared to the height of 0.560 inches of a standard 96 well or 384 well plate. Example dimensions provided herein are nonlimiting and are provided with a tolerance in dimension of about +/−0.010 inches.

Figure 7:
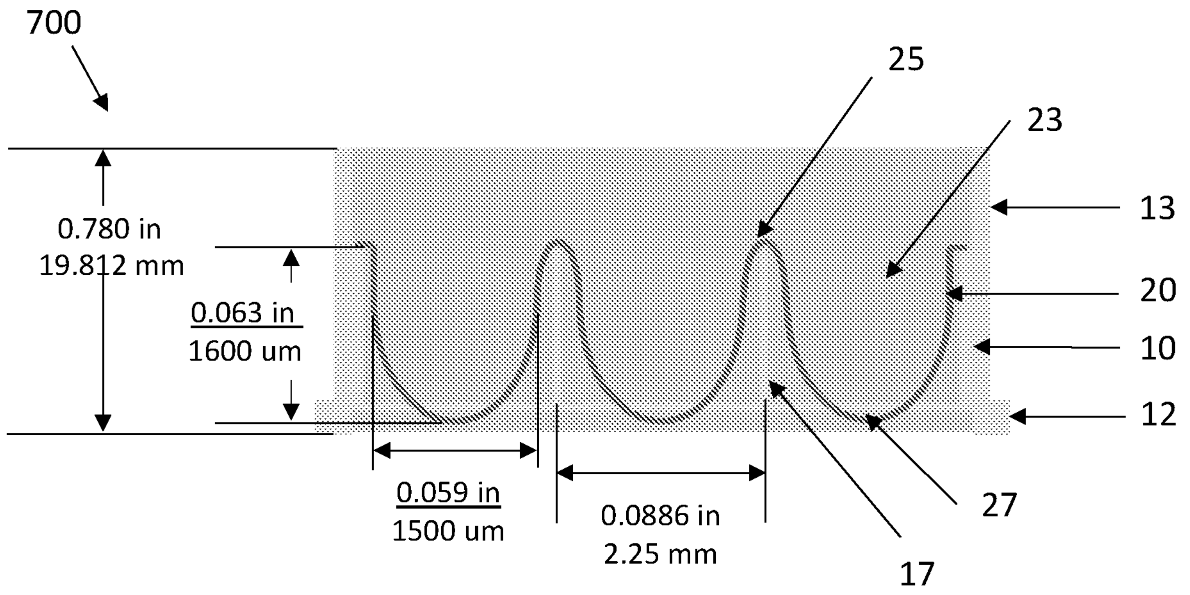
FIG. 7 shows a cross-sectional side view of a 1536 microcavity plate according to an embodiment of the disclosure.

FIG. 7 shows a cross-sectional side view of a portion of the 1536 microcavity plate. The portion of the microcavity plate 700 shows a molded bottom component or base 10 having an open well defined by sidewalls 13 and a bottom grid 17. The base 10 may have a flat bottom and a flange or skirt 12 around a perimeter of a bottom of the base 10. A dimpled microcavity substrate 20 is disposed within the base 10, wherein the individual microcavities 23 fit within openings in the bottom grid 17. The bottom grid 17 may comprise a plurality of grid segments ordered in rows and columns, each grid segment having a flat top and a flat bottom. The base 10 is further defined by an open well having sidewalls 13 extending vertically at a perimeter of the bottom grid, forming a perimeter around the bottom grid. The microcavity substrate 20 is disposed within the open well so that the plurality of microcavities 23 spaced in ordered rows and columns align with the openings of the bottom grid 10, which are arranged in ordered rows and columns in a grid format. In some embodiments, a height of the bottom grid may be about 0.060 inches. In some embodiments, a height of the bottom grid may be about 0.063 inches, and each opening of the bottom grid is about 0.0886 inches in length and about 0.0886 inches in width. The microcavity substrate 20 comprises microcavities 23 having curved or rounded bottoms 27 defining dimpled microcavities. Each microcavity comprises a cavity having a circular top opening portion and a rounded bottom. Each microcavity has a diameter of about 1500 μm and a depth of about 1600 μm. The microcavity substrate 20 is disposed within the open well so that each microcavity of the microcavity substrate is disposed in a center of an opening in the bottom grid. The bottom of the microcavities may lie above a bottom plane of the microcavity plate.

The microcavity substrate may be formed from a film. As a nonlimiting example, the microcavity substrate may be formed from a flat film having a thickness of 0.003-0.015 inches. The film may be formed of any suitable material, and nonlimiting examples include polystyrene, polymethylpentene, polyethylene, polypropylene, or laminates. A thickness at the rounded-bottom apex of the microcavity substrate may be in a range of about 35 microns to about 75 microns. Elsewhere, the thickness of the microcavity substrate may vary.

Figure 8:
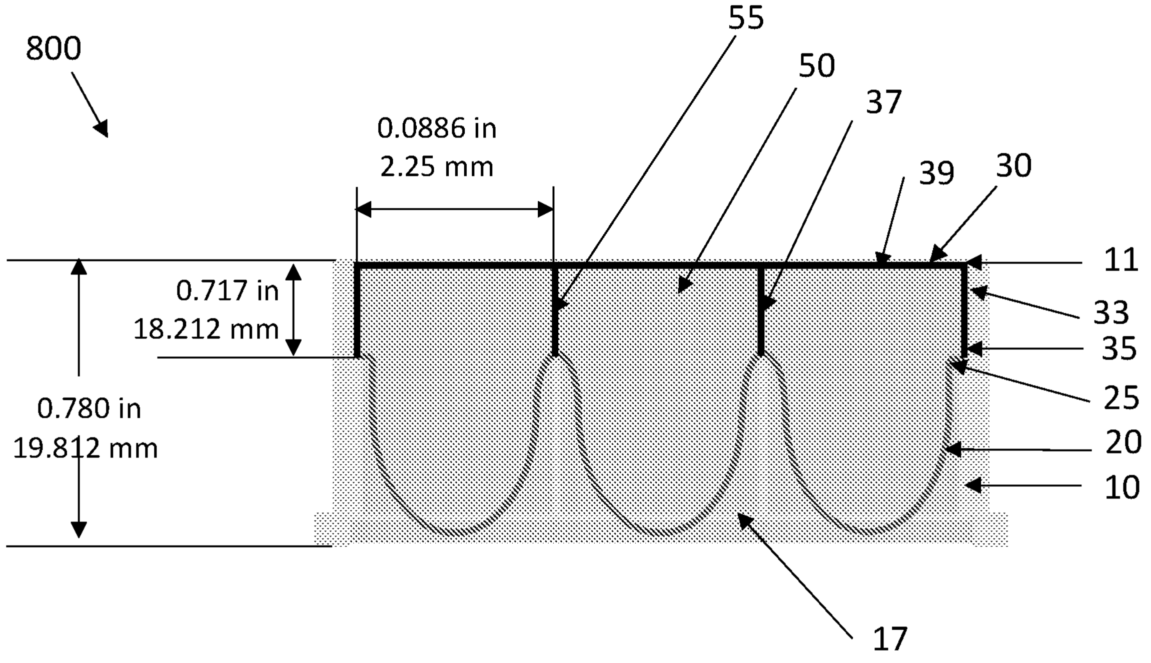
FIG. 8 shows a cross-sectional side view of a 1536 microcavity plate with grid according to an embodiment of the disclosure.

FIG. 8 shows a cross-sectional side view of a portion of the 1536 microcavity plate. The portion of the microcavity plate 800 shows an upper grid 30 placed within the open well of the base 10 on a top portion 25 of the microcavity substrate 20. The upper grid 30 may be added to the molded bottom component of the plate on top of the microcavity substrate 20 to define individual microcavity wells 50, wherein the segments of the upper grid define sidewalls 55 of the microcavity well 50. The upper grid 30 may be disposed within the open well so that a lower or bottom portion 35 of the upper grid 30 is in alignment with the lower grid of the microcavity plate and is disposed on a top portion 25 of the microcavity substrate 20, while a top portion 33 of the upper grid 30 extends to a top 11 of the base 10 or top of the open well sidewall. The upper grid 30 comprises ordered rows and columns defined by a plurality of grid segments in a first direction 37 and a plurality of grid segments in a perpendicular direction 39. In some embodiments, the upper grid has a height of about 0.717 inches. The grid segments of the upper grid 30 define a plurality of openings which are about 0.0886 inches in length and about 0.0886 inches in width, which mirrors the grid format of the bottom grid 17. The base may optionally include a flange or skirt 12 along an outer perimeter or edge of the microcavity plate, which may aid in stability of the plate.

Figure 9:
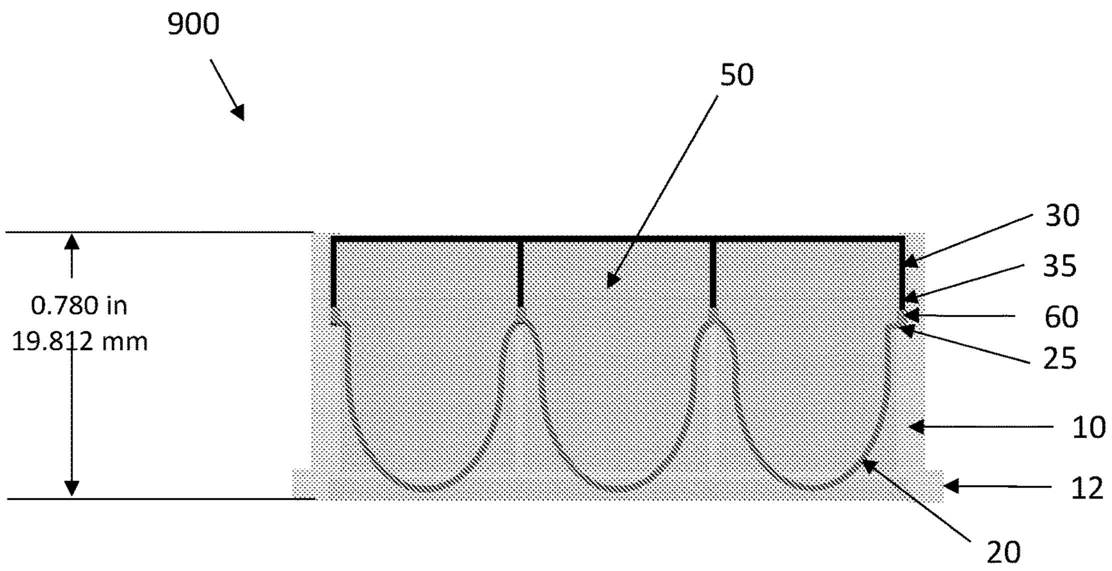
FIG. 9 shows a cross-sectional side view of a 1536 microcavity plate with grid and gasket according to an embodiment of the disclosure.

FIG. 9 shows a cross-sectional side view of a portion of the 1536 microcavity plate that includes a gasket sheet according to an embodiment of the invention. As shown in FIG. 9, a gasket material or gasket sheet 60 may be used to create a seal between wells 50. The gasket sheet 60 is disposed between a top portion 25 of the microcavity substrate 20 and a lower portion 35 of the upper grid 30. In embodiments, the gasket material or gasket sheet is formed from an elastomer. In some examples, the gasket sheet is formed from silicone. The gasket sheet may be used to create a seal where the upper grid comes in contact with a top of the microcavity substrate. For example, the seal may be created via compression by snapping the plates together or can be achieved via the use of an adhesive based gasket sheet made from a material such as a pressure sensitive adhesive. In some embodiments, snapping features are disposed at the perimeter of the two plates. In some embodiments, snapping features are disposed within the plate in the form of posts between 4 adjacent wells that are compression fitted together.

Figure 10:
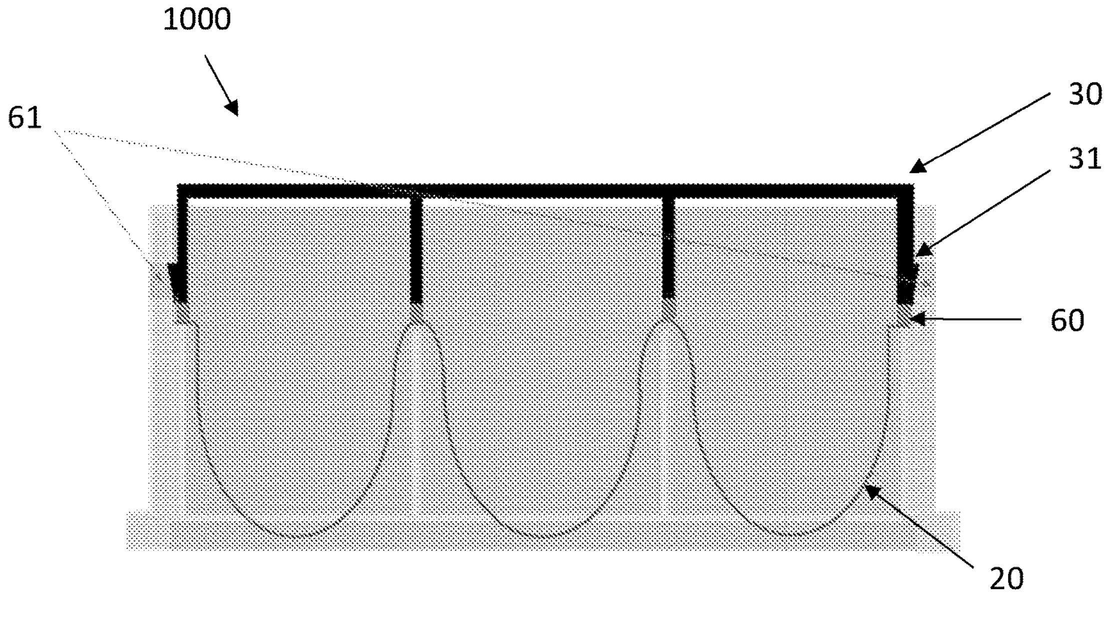
FIG. 10 shows a cross-sectional side view of a 1536 microcavity plate with grid and gasket according to an embodiment of the disclosure.

FIG. 10 shows a cross-sectional side view of a portion of the 1536 microcavity plate with a sealed upper grid 30 and gasket 60. The gasket material 60 is disposed between a lower portion 35 of the upper grid 30 and a top portion 25 of the microcavity substrate 20. The upper grid 30 comprises protrusions 31 around the perimeter of the upper grid 30. The protrusions 31 are configured to have a snap-fit to interlock with through holes 61 in the sidewalls 13 of the open well, or perimeter wall of the plate. When under compression or pressed into place, the protrusions on the upper grid clamp into the through holes in the plate perimeter wall and seal the upper grid to the portion of the plate, thereby transitioning the plurality of microcavities to a plurality of microcavity wells.

In some embodiments, the upper grid or top grid can be molded as a singular piece. In some embodiments, the bottom component can be molded as a singular piece, wherein the bottom component includes the base, bottom grid, and microcavity substrate. The gasket material may be overmolded on the top grid. In some embodiments, the bottom component may be formed by injection molding. The gasket material may be any suitable material, such as an elastomer. In some embodiments, the elastomer may be silicone. In some embodiments, the gasket material is a pressure sensitive adhesive.

The microcavity wells may have any suitable non-binding coating. For example, the coating may be a surface coating that is non-adherent to cells. In some embodiments, the cell non-adherent surface coating is a Corning Ultra Low Attachment (ULA) surface coating. The Corning ULA surface is hydrophilic, biologically inert and non-degradable, which promotes highly reproducible spheroid formation and easy harvesting. The covalent attachment of Ultra-Low Attachment surface reduces cellular adhesion to the well surface. The Ultra-Low Attachment (ULA) surface allows for uniform and reproducible 3D multicellular spheroid formation. The 1536 microcavity well format allows for high throughput 3D cell culture and analysis.

Microcavity plates according to embodiments described herein may be formed of any suitable material. In some examples, the plate may be formed in steps. For example, one step may be to construct the bottom component of the 1536 microcavity plate, wherein the bottom component comprises the base of the plate and the bottom grid portion. The material of construction may comprise a plastic polymer, co-polymer, or polymer blend. Nonlimiting examples include polystyrene, polypropylene, polyethylene, polyethylene terephthalate, polymethylpentene, polycarbonate, polymethyl methacrylate, styrene-butadiene copolymers, styrene-ethylene-butylene-styrene, other such polymers, or a combination thereof. Any suitable construction method may be used to form the bottom grid or base of the microplate. Nonlimiting examples include injection molding, thermoforming, 3D printing, or any other method suitable for forming a plastic part.

The microcavity substrate may be formed at the same time as a bottom grid portion. The microcavity substrate may be formed from the same material or a similar material and method for making the rest of the plate. In some embodiments, the microcavity substrate may be molded or formed separately from the rest of the plate and bonded subsequently through thermal-bonding, ultrasonic welding, or any other method of plastic joining. The material of construction for the microcavity substrate may comprise a plastic polymer, co-polymer, or polymer blend. Nonlimiting examples include polystyrene, polypropylene, polyethylene, polyethylene terephthalate, polymethylpentene, polycarbonate, polymethyl methacrylate, styrene-butadiene copolymers, styrene-ethylene-butylene-styrene polymers, other such polymers, or a combination thereof. Any suitable construction method may be used to form the microcavity substrate, such as nonlimiting examples include injection molding, thermoforming, 3D printing, or any other method suitable for forming a plastic part.

The upper grid may be formed using similar materials as the base or bottom grid and the microcavity substrate. In some embodiments, the upper grid is formed using more elastomeric materials such as natural rubbers, styrene-butadiene block copolymers, styrene-ethylene-butylene-styrene polymers, polyisoprene, polybutadiene, ethylene propylene rubber, ethylene propylene diene rubber, silicone elastomers, fluoroelastomers, polyurethane elastomers, and nitrile rubbers. Any suitable construction method may be used to form the upper grid of the microplate, such as nonlimiting examples include injection molding, thermoforming, 3D printing, or any other method suitable for forming a plastic part.

In some embodiments, the manufacture of the upper grid comprises an additional process to add an elastomer to the portion of the grid that will directly contact the substrate, if the upper grid is made from a non-elastomeric material. The elastomer facilitates a seal between the substrate and the upper grid to maintain the integrity of individual microcavity wells once the upper grid is in place. In such embodiments, the upper grid would be supplied separated from the microcavity plate and in its own packaging, as the upper grid would need to be kept sterile while the rest of the plate is used for cell culture.

According to embodiments of the present disclosure, methods for culturing cells or capturing cells on microcavity plate as described herein are also disclosed. In some embodiments, methods comprise cell culture of cell aggregates, or spheroids, in microcavity plate.

Embodiments of the disclosure further comprise methods of using a microcavity plate described herein. To use the 1536 microcavity plate, a user would make sure the upper grid is not within the microcavity plate before seeding cells in the microcavity plate. This would allow for ease of manual handling and maintenance of an initially homogenous culture environment. Once the culture has formed the required characteristics, such as number of cells or spheroids, differentiated state, etc., the cell culture medium in the plate would be removed. Note that the cell culture medium would be removed for the most part, as some cell culture medium would naturally remain in the individual microcavities with the spheroids. At that point, the upper grid could then be inserted, and medium or reagents may be added to perform HTS.

In an embodiment, a method of high-throughput screening comprises seeding cells in a microcavity plate; culturing the cells to form spheroids within the plurality of microcavities; attaching an upper grid to a top portion of the plurality of microcavities within the microcavity plate to form microcavity wells; and treating each of the microcavity wells as an individual for high throughput screening of the cultured spheroids. Culturing the cells may comprise contacting the cells in the microcavity plate with cell culture media.

Any type of cells may be cultured on the microcavity plate including, but not limited to, immortalized cells, primary culture cells, cancer cells, stem cells (e.g., embryonic or induced pluripotent), etc. The cells may be mammalian cells, avian cells, piscine cells, etc. The cells may be of any tissue type including, but not limited to, kidney, fibroblast, breast, skin, brain, ovary, lung, bone, nerve, muscle, cardiac, colorectal, pancreas, immune (e.g., B cell), blood, etc. The cells may be in any cultured form including disperse (e.g., freshly seeded), confluent, 2-dimensional, 3-dimensional, spheroid, etc.

Culturing cells on a microcavity plate may include seeding cells on the microcavity plate. Seeding cells on a microcavity plate may include contacting the plate with a solution containing the cells. Culturing cells on microcavity plate may further include contacting the microcavity plate with cell culture medium. Generally, contacting the microcavity plate with cell culture medium includes seeding or placing cells to be cultured on the microcavity plate in an environment with medium in which the cells are to be cultured. Contacting the microcavity plate with cell culture medium may include pipetting cell culture medium onto the microcavity plate. In some embodiments, cell culture medium may be disposed in the plate for a predetermined period of time, at least some of the cell culture medium may be removed after the predetermined period of time, and fresh cell culture medium may be added. Cell culture medium may be removed and replaced according to any predetermined schedule. For example, at least some of the cell culture medium may be removed and replaced every hour, or every 12 hours, or every 24 hours, or every 2 days, or every 3 days, or every 4 days, or every 5 days.

Any cell culture medium capable of supporting the growth of cells may be used. Cell culture medium may be for example, but is not limited to, sugars, salts, amino acids, serum (e.g., fetal bovine serum), antibiotics, growth factors, differentiation factors, colorant, or other desired factors. Exemplary cell culture medium includes Dulbecco's Modified Eagle Medium (DMEM), Ham's F12 Nutrient Mixture, Minimum Essential Media (MEM), RPMI Medium, Iscove's Modified Dulbecco's Medium (IMDM), MesenCult™-XF medium (commercially available from STEMCELL Technologies Inc.), and the like.

It will be appreciated that the various disclosed embodiments may involve particular features, elements, or steps that are described in connection with that particular embodiment. It will also be appreciated that a particular feature, element, or step, although described in relation to one particular embodiment, may be interchanged or combined with alternate embodiments in various non-illustrated combinations or permutations.

It is also to be understood that, as used herein the terms "the," "a," or "an," mean "at least one," and should not be limited to "only one" unless explicitly indicated to the contrary. Thus, for example, reference to "an opening" includes examples having two or more such "openings" unless the context clearly indicates otherwise.

All scientific and technical terms used herein have meanings commonly used in the art unless otherwise specified. The definitions provided herein are to facilitate understanding of certain terms used frequently herein and are not meant to limit the scope of the present disclosure.

As used herein, "have," "having," "include," "including," "comprise," "comprising," or the like are used in their open-ended sense, and generally mean "including, but not limited to."

Ranges may be expressed herein as from "about" one particular value, and/or to "about" another particular value. When such a range is expressed, examples include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

All numerical values expressed herein are to be interpreted as including "about," whether or not so stated, unless expressly indicated otherwise. It is further understood, however, that each numerical value recited is precisely contemplated as well, regardless of whether it is expressed as "about" that value. Thus, "a dimension less than 10 mm" and "a dimension less than about 10 mm" both include embodiments of "a dimension less than about 10 mm" as well as "a dimension less than 10 mm."

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a method comprising A+B+C include embodiments where a method consists of A+B+C, and embodiments where a method consists essentially of A+B+C.

Although multiple embodiments of the present disclosure have been described in the Detailed Description, it should be understood that the disclosure is not limited to the disclosed embodiments, but is capable of numerous rearrangements, modifications and substitutions without departing from the disclosure as set forth and defined by the following claims.

What is claimed is:

1. A microcavity plate comprising:

a base comprising:

a bottom grid comprising a plurality of grid segments arranged in ordered rows and columns to form a plurality of openings, a plurality of sidewalls extending vertically from a bottom surface to a top surface, the plurality of sidewalls having a lower portion, an upper portion, and an inner rim located at a junction of the lower and upper portions, the lower portion of the plurality of sidewalls defining a bottom grid perimeter around the bottom grid, and an open well defined by the upper portion of the plurality of sidewalls;

a microcavity substrate comprising a plurality of microcavities arranged in ordered rows and columns that align with the plurality of openings in the bottom grid, each microcavity comprising a cavity disposed within an opening of the plurality of openings of the bottom grid; and an upper grid removably received in the open well such that a lower portion of the upper grid rests on the inner rim, the upper grid comprising a plurality of upper grid segments that form a plurality of well openings, the upper grid segments being arranged in ordered rows and columns that mirror the ordered rows and columns of the bottom grid such that the plurality of well openings are aligned with the plurality of openings.

2. The microcavity plate of claim 1, wherein the upper grid is configured for placement in the open well on top of the bottom grid delineating the ordered rows and columns of the base.

3. The microcavity plate of claim 2, wherein the plurality of well openings align with the plurality of microcavities in the microcavity substrate.

4. The microcavity plate of claim 3, further comprising a plurality of microcavity wells formed when the upper grid is received in the open well, each microcavity well being defined by a well opening of the plurality of well openings and an associated and aligned microcavity of the plurality of microcavities.

5. The microcavity plate of claim 2, further comprising a gasket material.

6. The microcavity plate of claim 5, wherein the gasket material is integrated on the lower portion of the upper grid, wherein when the upper grid is inserted in the open well, the gasket material is disposed between the lower portion of the upper grid and a top of the microcavity substrate.

7. The microcavity plate of claim 1, wherein the plurality of microcavities comprises 1536 individual microcavities.

8. The microcavity plate of claim 1, wherein each cavity in the plurality of microcavities comprises a top surface and a rounded bottom.

9. The microcavity plate of claim 8, wherein a diameter of each cavity at the top surface of the microcavity is about 1500 μm.

10. The microcavity plate of claim 8, wherein an inner surface of each cavity is coated with a coating non-adherent to cells.

11. The microcavity plate of claim 10, wherein the coating comprises an ultra low attachment (ULA) surface coating.

12. The microcavity plate of claim 2, wherein the upper grid comprises a plurality of protrusions extending from a perimeter of the upper grid.

13. The microcavity plate of claim 12, wherein protrusions in the plurality of protrusions are configured to align and interlock with a plurality of through holes in the sidewalls of the open well.

14. The microcavity plate of claim 1, wherein the microcavity substrate is formed from polymers selected from polystyrene, polypropylene, polyethylene, polyethylene terephthalate, polymethylpentene, polycarbonate, polymethyl methacrylate, styrene-butadiene copolymers, styrene-ethylene-butylene-styrene, other such polymers, and a combination thereof.

15. The microcavity plate of claim 14, wherein the microcavity substrate is formed from polystyrene.

16. The microcavity plate of claim 1, wherein the base is formed from a polymer comprising polystyrene, polypropylene, polyethylene, polyethylene terephthalate, polymethylpentene, polycarbonate, polymethyl methacrylate, styrene-butadiene copolymers, styrene-ethylene-butylene-styrene, other such polymers, and a combination thereof.

17. The microcavity plate of claim 16, wherein the base is formed from polystyrene.

18. The microcavity plate of claim 1, wherein the upper grid is formed from elastomeric materials selected from natural rubbers, styrene-butadiene block copolymers, styrene-ethylene-butylene-styrene polymers, polyisoprene, polybutadiene, ethylene propylene rubber, ethylene propylene diene rubber, silicone elastomers, fluoroelastomers, polyurethane elastomers, nitrile rubbers, and a combination thereof.

19. The microcavity plate of claim 5, wherein the gasket material is formed from an elastomer.

20. The microcavity plate of claim 19, wherein the elastomer comprises silicone.

21. The microcavity plate of claim 5, wherein the gasket material is formed from a pressure sensitive adhesive.

22. The microcavity plate of claim 1, wherein the microcavity plate is used for cell culture of spheroids.

23. The microcavity plate of claim 1, wherein the microcavity plate is used for high-throughput screening.

24. A method of high-throughput screening comprising:

seeding cells in a microcavity plate of claim 1;

culturing the cells to form spheroids within the plurality of microcavities;

attaching the upper grid to a top portion of the plurality of microcavities within the microcavity plate to form microcavity wells; and treating each of the microcavity wells as an individual for high throughput screening of the cultured spheroids.

25. The method of claim 24, wherein culturing the cells comprises contacting the cells in the microcavity plate with cell culture media.

* * * * *